United States Patent [19]

Raghu et al.

[11] 4,339,603

[45] Jul. 13, 1982

[54] PROCESS FOR CONVERTING OPTICALLY ACTIVE L-N-(2-AMINO-2-PHENETHYL)-2-METHOXYETHYLAMINE TO THE CORRESPONDING DL-DERIVATIVE

[75] Inventors: Sivaraman Raghu, Norwalk; Arnold Zweig, Westport, both of Conn.

[73] Assignee: American Cyanamid Company, Stamford, Conn.

[21] Appl. No.: 1,807

[22] Filed: Jan. 8, 1979

[51] Int. Cl.$^3$ ............................................. C07C 20/00
[52] U.S. Cl. ............................... 564/302; 260/571.1; 548/351; 564/220; 564/372
[58] Field of Search .................. 260/571.5 P; 564/302

[56] References Cited

U.S. PATENT DOCUMENTS

| | | | |
|---|---|---|---|
| 2,514,380 | 7/1950 | Duschinsky | 260/570.5 X |
| 3,184,460 | 5/1965 | Akkerman et al. | 260/570.5 X |
| 3,845,070 | 10/1974 | McMenim | 260/570.5 X |
| 3,923,808 | 12/1975 | Gelder et al. | 260/570.5 X |

*Primary Examiner*—Robert V. Hines
*Attorney, Agent, or Firm*—Gordon L. Hart

[57] ABSTRACT

There is provided a process for racemizing an undesirable, optically active compound for conversion to levamisole, namely, l-N-(2-amino-2-phenethyl)-2-methoxyethylamine, by converting the latter to optically active 1-(2-methoxyethyl)-4-phenyl-2-imidazolidone, which is next converted to the corresponding optically inactive imidazolidone derivative, which derivative is hydrolyzed to the optically inactive racemate, dl-N-(2-amino-2-phenethyl)-2-methoxyethylamine. The latter can be resolved to obtain the d and l components of the racemate, the d component being utilized directly in levamisole synthesis and the l component being again subjected to the above procedure.

5 Claims, No Drawings

METHOD FOR THE PREPARATION OF CYCLOHEXANOL AND/OR CYCLOHEXANONE

This application is a continuation-in-part of Ser. No. 171,034, filed July 22, 1980, now abandoned.

BACKGROUND OF THE INVENTION

The invention relates to an improvement to a method for the preparation of cyclohexanol and/or cyclohexanone by the steps of hydrogenating benzene to cyclohexene, hydrating cyclohexene thus obtained to cyclohexanol and/or oxidating it to cyclohexanone, recovering product cyclohexanol and/or cyclohexanone, and returning unconverted benzene and/or cyclohexene to the hydrogenation step.

Such a method is known from Japanese Patent application No. 53,090,242, which application has been laid open to inspection (Derwent Abstract No 65968A), for the preparation of cyclohexanone. However, a serious problem is encountered in practicing this known method in that by-product cyclohexane is also formed in the hydrogenation of benzene to cyclohexene, unless a low degree of benzene conversion is applied. Such a low degree of benzene conversion is generally not economically justifiable.

Therefore, in the known method, cyclohexane must be separated from the benzene-cyclohexene-cyclohexane containing mixture remaining after recovery of cyclohexanol from the hydration reaction mixture and/or of cyclohexanone from the oxidation reaction mixture prior to recycle of the remaining benzene-cyclohexene containing mixture to the hydrogenation step. However, cyclohexane is very difficult to separate from mixtures containing benzene and/or cyclohexene, and requires relatively expensive separation techniques such as extractive distillation. This is due to the azeotrope formation between benzene, cyclohexene, cyclohexane and/or water.

Faced with this choice, it is generally preferable when practicing the known method to maintain the degree of benzene conversion relatively low, for instance lower dan 10% in order to permit only a minimum quantity of cyclohexane to be formed. However, whether such a low degree of conversion is utilized, or benzene separation is effected by expensive methods such as extractive distillation, an economic process for the preparation of cyclohexanol and/or cyclohexanone from benzene has not been achieved.

SUMMARY OF THE INVENTION

An objective of the present invention is to provide an improvement to the known method for the preparation of cyclohexanol and/or cyclohexanone from benzene rendering such method more economically attractive. A further objective is to provide an improvement to the known method for the preparation of cyclohexanol and/or cyclohexanone from benzene which permits utilization of an economically attractive degree of benzene conversion while at the same time avoiding the necessity of employing expensiv separation techniques to remove cyclohexane from benzene prior to recycle.

According to the present invention, cyclohexanol and/or cyclohexanone are prepared by the steps of (a) hydrogenating benzene in a hydrogenation zone to a hydrogenation reaction mixture containing cyclohexene, unreacted benzene, and by-product cyclohexane (b) hydrating cyclohexene contained in the hydrogenation reaction mixture in a hydration zone to form a hydration reaction mixture containing cyclohexanol, unreacted benzene, by-product cyclohexane, and possibly unreacted cyclohexene and/or oxidating it in an oxidation zone to form an oxidation reactor mixture containing cyclohexanone, unreacted benzene, by-product cyclohexane, and possibly unreacted cyclohexene, and (c) recovering product cyclohexanol from the hydration reaction mixture and/or product cyclohexanone from the oxidation reaction mixture, and an organic phase contaiing unreacted benzene, by-product cyclohexane, and possibly cyclohexene. The improvement of the present invention comprises introducing the organic phase separated from the hydration and/or oxidation reaction mixture into a dehydrogenation zone wherein by-product cyclohexane and cyclohexene if present is dehydrogenated to benzene. The benzene thus formed is thereafter recycled to the hydrogenation zone, together with the unreacted benzene contained in the hydration reaction mixture.

The improved method of the invention has the great advantage over the known methods that the difficult separation of cyclohexane from mixtures containing benzene and/or cyclohexene can be dispensed with. Losses of expensive extractive distillation agents are thus avoided. Furthermore, there is no by-product cyclohexane remaining for which a use must be found. Moreover, a higher degree of benzene conversion can be applied in the hydrogenation step so that a more economically attractive process operation becomes possible.

The hydrogenation of benzene to cyclohexene can be carried out by any known method. Such a suitable method is described, for instance, in German Offenlegungsschrift No. 2,221,137, the disclosure of which is hereby incorporated by reference. According to this known method, the hydrogenation is carried out at a hydrogen pressure of about 10 to 50,000 kPa, and at a temperature of between 0° and 250° C. in the presence of water and an alkaline agent such as an aqueous alkali hydroxide solution. Suitable catalysts for the hydrogenation of benzene to cyclohexene include particularly ruthenium, rhodium and palladium compounds, ruthenium compound or reduction products thereof being particularly preferable. It is preferable that relatively high degrees of benzene conversion which would result in a hydrogenation reaction product containing from about 25 to 75 mole-percent of cyclohexane. Preferably, the degree of benzene conversion is at least 30 percent, and most preferably is in the range of from about 40 to 80 percent.

The hydration of cyclohexene to cyclohexanol can also be effected by any of the known methods. Most generally an acid catalyst is used in the hydration process. Very suitable methods are described in British Pat. Nos. 1,381,149 and 1,542,996, which are incorporated herein by reference.

Sulfuric acid has been found to be a very suitable catalyst for the hydration reaction, and ferrous sulphate can be used as a co-catalyst. The hydration process is most generally carried out in a sequence of process steps involving (1) the addition of the acid to the double bond of the cyclohexene, thus forming an ester of cyclohexanol and the acid, for example, cyclohexyl hydrogen sulphate, and (2) hydrolysis of the cyclohexyl ester to cyclohexanol and the acid. The first, ester forming, step can be carried out at temperatures in the range of, e.g., between −50° C. and +30° C., although temperatures in the range of 30° to 100° C. may also be utilized. The second, hydrolysis, step can be suitably carried out at a temperature in the range of between about 50° and 150° C.

Catalysts other than sulfuric acid can also be used for the hydration of cyclohexene. For example, a strongly acid ion exchanger can be used, such as a cross-linked polystyrene resin containing sulphonic acid groups, or phosphoric acid.

The hydration of cyclohexene may be effected in the presence of the unreacted benzene and by-product cyclohexane present in the hydrogenation reaction mixture. Thus, there is no need for the separation of cyclohexene prior to the hydration step.

The reaction mixture from the hydration reactor generally comprises an aqueous phase, and an organic phase containing cyclohexanol and lower boiling organic constituents including benzene, cyclohexane, and possibly unconverted cyclohexene.

The oxidation of cyclohexene to cyclohexanone can be effected by any of the known methods as well. A very suitable method is described in Angewandte Chemie, 71 (5), page 176 and following pages which is incorporated herein by reference.

An acid aqueous solution of $PdCl_2$ has been found to be a very suitable catalyst for the oxidation reaction, and e.g. $CuCl_2$, $Fe_2(SO_4)_3$, $K_2Cr_2O_8$ and $K_2S_2O_8$ can be used as a co-catalyst. The oxidation process is most generally carried out in sequence of process steps involving (1) oxidation of cyclohexene to cyclohexanone by reaction of cyclohexene with the catalyst solution in which the catalyst is reduced, (2) separating of the organic phase from the reaction mixture, (3) bringing the catalyst back in the oxidated state by means of an oxygen containing gas (e.g. air), (4) recirculating the catalyst to the first step. The first step can be carried out at a temperature of between 0° and 150° C. and a pressure of between 0.05 and 5 MPa. The third step can be carried out at a temperature of between 0° and 250° C. and at a pressure of between 0.05 and 200 MPa.

The oxidation of cyclohexene may be effected in the presence of the unreacted benzene and by-product cyclohexane present in the hydrogenation reaction mixture. Thus, there is no need for the separation of cyclohexene prior to the oxidation step.

The reaction mixture from the oxidation reactor generally comprises an aqueous phase, and an organic phase containing cyclohexanone and lower boiling organic constituents including benzene, cyclohexane, and possibly unconverted cyclohexene.

After separation of the aqueous phase from the hydration and/or oxidation reaction mixture, cyclohexanol and/or cyclohexanone is recovered from the organic phase by, for example, distillation. This distillation of the organic phase also produced a lower boiling or lighter fraction or mixture comprised of benzene, cyclohexane, and possibly cyclohexene, which organic mixture has a boiling point lower than that of cyclohexanol and/or cyclohexanone.

In accordance with the method of the present invention, it is not necessary to carry out the difficult separation of this lighter organic mixture into its components. To the contrary, this mixture obtained from the hydration and/or oxidation zone can be fed as a whole to the dehydrogenation zone wherein the cyclohexane is dehydrogenated to benzene. Furthermore, cyclohexene, which may also be present, is converted in this step into benzene as well.

This dehydrogenation can be carried out, for instance, in the gas phase in the presence of a catalyst containing an element selected from Group VI or Group VIII of the Periodic Table of Elements, such as chronium, molybdenum, nickel, palladium, or platinum. Suitable catalysts for carrying out this dehydrogenation step include, for example platinum/aluminum oxide, platinum/carbon, molybdic oxide/aluminum oxide, chromic oxide/aluminum oxide, and palladium nickel alloy. Preferably, this dehydrogenation reaction is carried out at a temperature in the range of between about 200 and 650° C., and at a pressure of between about 10 and 1,000 kPa. Dehydrogenation processes which are very suitable for use in accordance with the present invention are disclosed in U.S. Pat. Nos. 3,682,838 and 3,752,776, which references are incorporated herein by reference.

The benzene thus obtained by the dehydrogenation reaction is returned to the hydrogenation zone, together with the unreacted benzene that was present in the dehydrogenation zone. In recycling this benzene to the hydrogenation zone, it may be necessary to remove certain undesired by-products, such as methyl cyclopentane, e.g. by draining, in order to prevent the accumulation thereof. Additionally, the hydrogen which is obtained in the dehydrogenation step may be returned to the hydrogenation zone.

The crude cyclohexanol obtained from the hydration zone can be further purified by distillation. If desired, the cyclohexanol can be dehydrogenated by a known method to form cyclohexanone, which in turn can be used as a feedstock for the preparation of caprolactam. The crude cyclohexanone obtained from the oxidation zone can be further purified also by distillation.

DETAILED DESCRIPTION OF TWO PREFERRED EMBODIMENTS

The invention will be further elucidated by the following process detailed description with reference to the figures. The description and figures are representatives of two preferred embodiments, and it should be understood that different configurations and variations of equipment, flows, and conditions may be made with the scope of the present invention. In both figures the same numbers mean the same.

Figure 1:
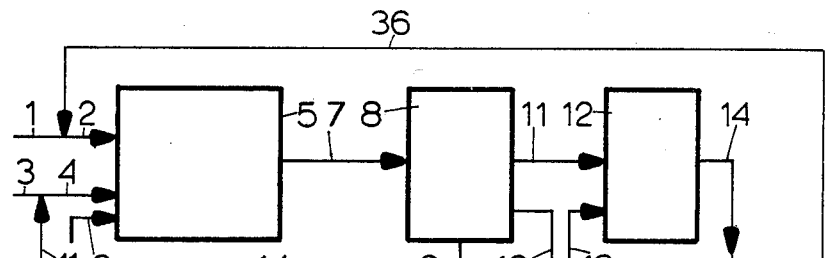
FIG. 1, illustrates an embodiments of the invention for the preparation of cyclohexanol from benzene.

FIG. 1: Hydrogen and benzene are fed to hydrogenation reactor 5 through lines 1–2 and through lines 3–4 respectively. Benzene is hydrogenated in reactor 5 at a temperature of 200° C. and at a pressure of about 22 MPa with the aid of a ruthenium-titanium-zinc catalyst supplied to the reactor through line 6.

The catalyst used has been obtained by the conversion of one part by weight of $RuCl_3.3\ H_2O$ with 1.2 parts by weight of $TiCl_3$, 1 part by weight of $ZnCl_2$ and 65 ml water, followed by the addition of 15 ml of a 20 N aqueous sodium hydroxide solution.

The hydrogenation is carried out in hydrogenation reactor 5 in the liquid phase at a hydrogen pressure of 20 MPa. The degree of benzene conversion is 57 percent, while 53 percent of the converted benzene is converted into cyclohexene and the remainder almost completely into cyclohexane. Non-converted hydrogen is recirculated (not shown). The hydrogenation reactor product thus obtained contains about 30 mole-percent cyclohexene and about 26 mol-percent cyclohexane.

The liquid mixture obtained from reactor 5 is passed through line 7 to separator 8. Separator 8 serves the purpose of recovering the catalyst by filtration, and the liquid mixture is separated into an organic hydrogenation reaction mixture phase and an aqueous phase. The catalyst is recovered through line 9, and the aqueous phase is carried out off through line 10.

The organic hydrogenation reaction mixture is fed through line 11 to the hydration zone wherein it is introduced into sulphuric acid addition reactor 12. A 60 percent by weight aqueous sulphuric acid solution containing 1 percent by weight of ferrous sulphate is fed through line 13 to reactor 12. The addition reaction is effected, with reflux cooling, at 80° C. and atmospheric pressure, and at a cyclohexene/sulphuric acid molar ratio of 0.5 to 1.

The resulting mixture is subsequently fed from reactor 12, through line 14, to ester hydrolysis reactor 15. Sufficient water is fed into reactor 15 through line 16 such that the sulphuric acid concentration is lowered to 30 percent by weight. The ester hydrolysis is carried out in reactor 15 at 110° C. and at atmospheric pressure. The liquid product mixture obtained from reactor 15 is separated in a separator (not illustrated) into an organic layer consisting of crude cyclohexanol and an aqueous layer containing sulphuric acid. Non-converted cyclohexene, benzene, and cyclohexane leave hydrolysis reactor 15 as a vaporous azeotropic mixture with water.

The organic layer consisting of crude cyclohexanol, together with a cyclohexanone containing mixture discussed below, is fed through line 17–18 to distillation column 19. Here a light fraction of constituents having a boiling point lower than that of cyclohexanol and cyclohexanone is distilled off and carried off through line 20. The distillation residue passes through line 21 to a second distillation column 22, where pure cyclohexanone is distilled off and recovered through line 23. The distillation residue from this second column is fed through line 24 to a third distillation column 25. Here pure cyclohexanol is distilled off, which is carried off through line 26. A distillation residue leaves the system through line 27.

If desired, the cyclohexanol can be extracted, in whole or in part, through line 28. However, in this example, the cyclohexanol passes through line 26A to alcohol dehydrogenation unit 29, wherein it is partly dehydrogenated to cyclohexanone by a known method, for example, using a zinc or copper catalyst. The hydrogen obtained is separated off and returned (through a line not shown) to hydrogenation reactor 5. The cyclohexanol/cyclohexanone mixture obtained in unit 29 passes through lines 30 and 18 to distillation column 19.

The aqueous layer of the product mixture from ester hydrolysis reactor 15 is carried off through line 31. If necessary, the sulphuric acid contained in this aqueous phase is concentrated, for instance by evaporation, and returned to sulphuric acid addition reactor 12.

The vaporous mixture of cyclohexene, benzene, cyclohexane, and water is fed from addition reactor 12 through line 32 to dehydrogenation reactor 33. Here cyclohexane and cyclohexene are dehydrogenated to benzene at 370° C. and atmospheric pressure in the presence of 0.6 percent by weight of platinum on aluminum oxide as catalyst. The degree of conversion of the cyclohexane is about 98 percent, and that of cyclohexene virtually 100 percent. The conversion efficiency is about 98 percent.

The resulting mixture is fed from reactor 33 through line 34 to condensor/separator 35. The non-condensed gas, mainly hydrogen, is returned through lines 36 and 2 to hydrogen reactor 5. The aqueous phase of the condensate is carried off through line 37, and the organic phase is fed through line 38 to distillation column 39. Here a light fraction consisting mainly of methyl cyclopentane by-product, with some benzene carried along azeotropically, is distilled off and discharged from the system to line 40. The distillation residue consisting mainly of benzene is returned, through lines 41 and 4, to hydrogenation reactor 5. If desired, the benzene can first be separated by distillation from some heavier impurities prior to recycle to hydrogenation reactor 5.

Figure 2:
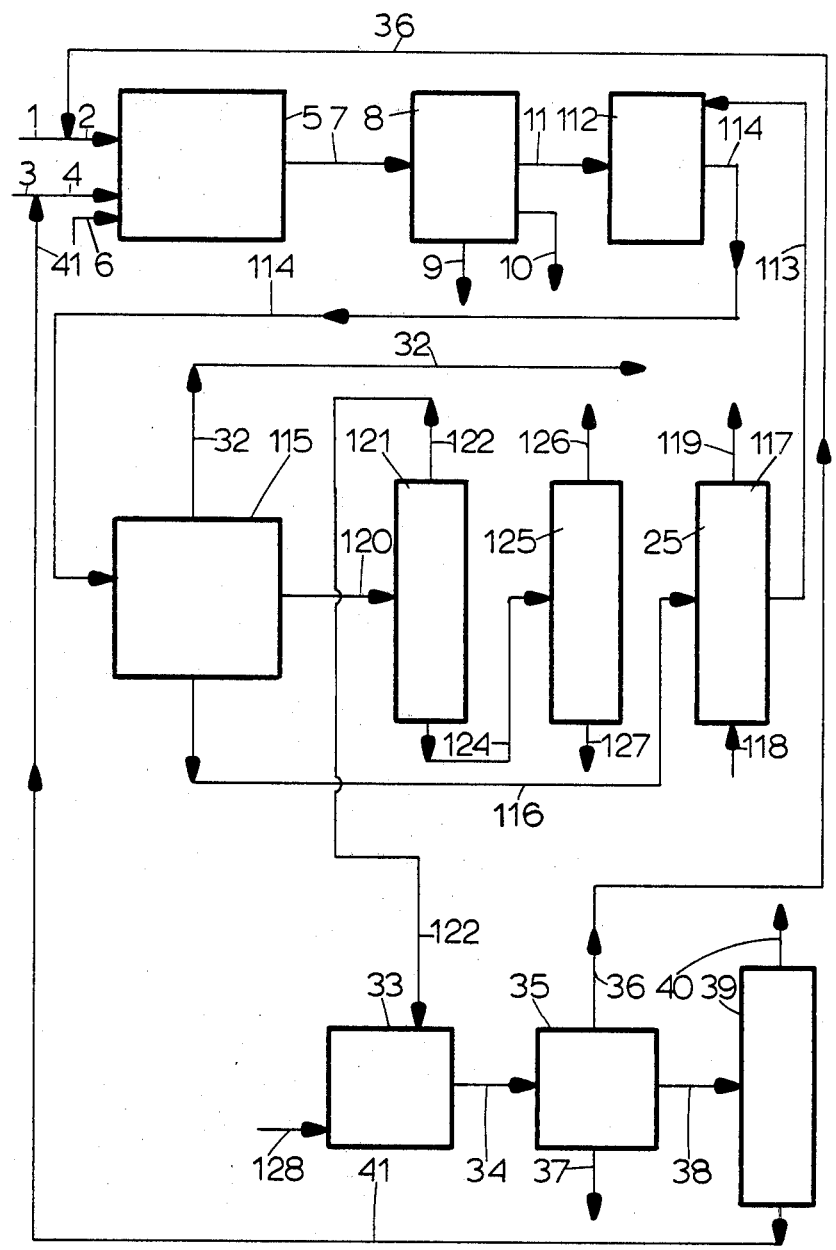
FIG. 2 illustrates an embodiment of the invention for the preparation of cyclohexanal from benzene.

FIG. 2: The first (hydrogenation) and the last (dehydrogenation) section are the same as described in FIG. 1. In the embodiment of FIG. 2 the hydration section of FIG. 1 is replaced by an oxidation section. Therefore only this oxidation section is described here.

Now the organic phase from separator 8 is fed, through line 11, to oxidation reactor 112. Through line 113 an aqueous solution is fed to reactor 112, containing $PdCl_2$ and $CuCl_2$. The pH of this solution is between $-2$ and $+4$. The oxidation reaction is carried out at 100° C. under autogenic pressure. The molar ratio between cyclohexene and $PdCl_2$ of the supply to 112 is 100:1.

The resulting mixture is then fed to separator 115 through line 114, where the catalyst containing aqueous phase is separated from the organic phase. The aqueous catalyst solution is fed to reoxidation reactor 117 through line 116. Through line 118 air is fed to reactor 117. The reoxidation is carried out at 100° C. and 1 MPa. The reoxidized catalyst solution is recirculated to oxidation reactor 112 through line 113. The exhausted air is blown off through line 119.

The organic phase from separator 115 is fed to distillation unit 121 through line 120. Here a mixture of benzene, cyclohexene and cyclohexane is distilled off. The bottom product of distillation unit 121 is fed to a second distillation column 125 through line 124. Here pure cyclohexanone is distilled off and is recovered through line 126. The distillation residue of 125 leaves the system through line 127. The benzene-cyclohexene-cyclohexane mixture from 121 is fed to dehydrogenation reactor 33 through line 122. If wanted steam may be supplied to 33 via line 128.

From here the description of FIG. 2 is the same again as the description of FIG. 1 (see above).

What is claimed is:

1. A method for the preparation of cyclohexanone from benzene by the steps of:
   hydrogenating benzene in the presence of hydrogen and a hydrogenation catalyst in a hydrogenation zone to form a hydrogenation reaction mixture containing cyclohexene, by-product cyclohexane, and unreacted benzene;
   oxidizing cyclohexene contained in said hydrogenation reaction mixture to cyclohexanone in an oxidation zone in the presence of an oxygen containing gas and an oxidation catalyst to form an oxidation reaction mixture containing cyclohexanone, by-product cyclohexane and unreacted benzene;
   separating from said oxidation reaction mixture product cyclohexanone, and an organic phase containing by-product cyclohexane and unreacted benzene;

the improvement comprising introducing said organic phase into a hydrogenation zone wherein by-product cyclohexane contained in said organic phase is dehydrogenated to benzene, and recycled to said hydrogenation zone.

2. The method of claim 1 wherein, in said hydrogenation zone, the degree of benzene conversion is such that the hydrogenation reaction mixture contains from about 25 to 75 mole-percent of cyclohexane.

3. The method of claims 1 or 2 wherein, in said hydrogenation zone, a ruthenium catalyst is used, and the degree of benzene conversion is at least 30 percent.

4. The method of claim 3 wherein, in said hydrogenation zone, the degree of benzene conversion is between 40 and 80 percent.

5. The method of claim 1 wherein hydrogen obtained from said dehydrogenation zone is recycled to said hydrogenation zone.

6. A method for the preparation of cyclohexanol from benzene by the steps of:

hydrogenating benzene in the presence of hydrogen and a hydrogenation catalyst in a hydrogenation zone to form a hydrogenation reaction mixture containing cyclohexene, by-product cyclohexane, and unreacted benzene;

hydrating cyclohexene contained in said hydrogenation reaction mixture to cyclohexanol in a hydrating zone in the presence of water and a hydrating catalyst to form a hydration reaction mixture containing cyclohexanol, by-product cyclohexane, and unreacted benzene;

separating from said hydration reaction mixture product cyclohexanol and an organic phase containing by-product cyclohexane and unreacted benzene;

the improvement comprising introducing said organic phase into a dehydrogenation zone wherein by-product cyclohexane contained in said organic phase is dehydrogenated to benzene, and recycled to said hydrogenation zone.

7. The method of claim 6 wherein, in said hydrogenation zone, the degree of benzene conversion is such that the hydrogenation reaction mixture contains from about 25 to 75 mole-percent of cyclohexane.

8. The method of claims 6 or 7 wherein, in said hydrogenation zone, a ruthenium catalyst is used, and the degree of benzene conversion is at least 30 percent.

9. The method of claim 8 wherein, in said hydrogenation zone, the degree of benzene conversion is between 40 and 80 percent.

10. The method of claim 6 wherein hydrogen obtained from said dehydrogenation zone is recycled to said hydrogenation zone.

11. The method of claim 1 or 6 wherein said organic phase introduced into said dehydrogenation zone additionally contains unreacted cyclohexene which is dehydrogenated to benzene, and recycled to said hydrogenation zone.

12. The method of claim 1 or 6 wherein said dehydrogenation is conducted at a temperature of about 200° C. to 650° C. and at a pressure of about 10 kPa to 1000 kPa.

13. The method of claim 1 or 6 wherein said dehydrogenation is carried out in the gas phase in the presence of a catalyst containing an element selected from Group VI and Group VIII of the periodic table.

14. The method according to claim 13 wherein said element is selected from the group consisting of chromium, molybdenum, nickel, palladium and platinum.

15. The method of claim 13 wherein said catalyst is selected from the group consisting of platinum/aluminium oxide, platinum/carbon, molybdic oxide/aluminium oxide, chromic oxide/aluminium oxide and palladium nickel alloy.

* * * * *